United States Patent [19]

Ferguson et al.

[11] Patent Number: 5,230,802
[45] Date of Patent: Jul. 27, 1993

[54] EXTRACTION PROCESS USING A NOVEL ORGANIC ACID AS A LIQUID ION EXCHANGER

[75] Inventors: Robert N. Ferguson; Charles R. Howe, both of Richmond; Henry V. Secor, Midlothian; Jeffrey I. Seeman, Richmond, all of Va.

[73] Assignees: Philip Morris Incorporated, New York, N.Y.; Philip Morris Products Inc., Richmond, Va.

[21] Appl. No.: 902,426

[22] Filed: Jun. 24, 1992

Related U.S. Application Data

[63] Continuation of Ser. No. 700,402, May 15, 1991, abandoned.

[51] Int. Cl.$^5$ .............................................. B01D 61/28
[52] U.S. Cl. ................................ 210/644; 210/500.23
[58] Field of Search ............... 210/638, 643, 644, 634, 210/500.27, 500.23; 426/653; 514/653, 651, 210, 431; 564/267

[56] References Cited

U.S. PATENT DOCUMENTS 4,132,682 1/1979 Seita et al. .................. 210/500.27 X
4,200,569 4/1980 Ladbrooke et al. ............ 426/653 X Primary Examiner—Frank Spear
Attorney, Agent, or Firm—James E. Schardt

[57] ABSTRACT

This invention provides novel organic acids which exhibit utility as liquid ion exchanges suitable for use in an invention solvent extraction process. Illustrative of an invention organic acid is a compound corresponding to the formula:

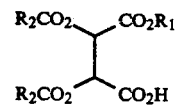

where each of $R_1$ and $R_2$ is a $C_3$–$C_{16}$ branched alkyl group.

9 Claims, 1 Drawing Sheet

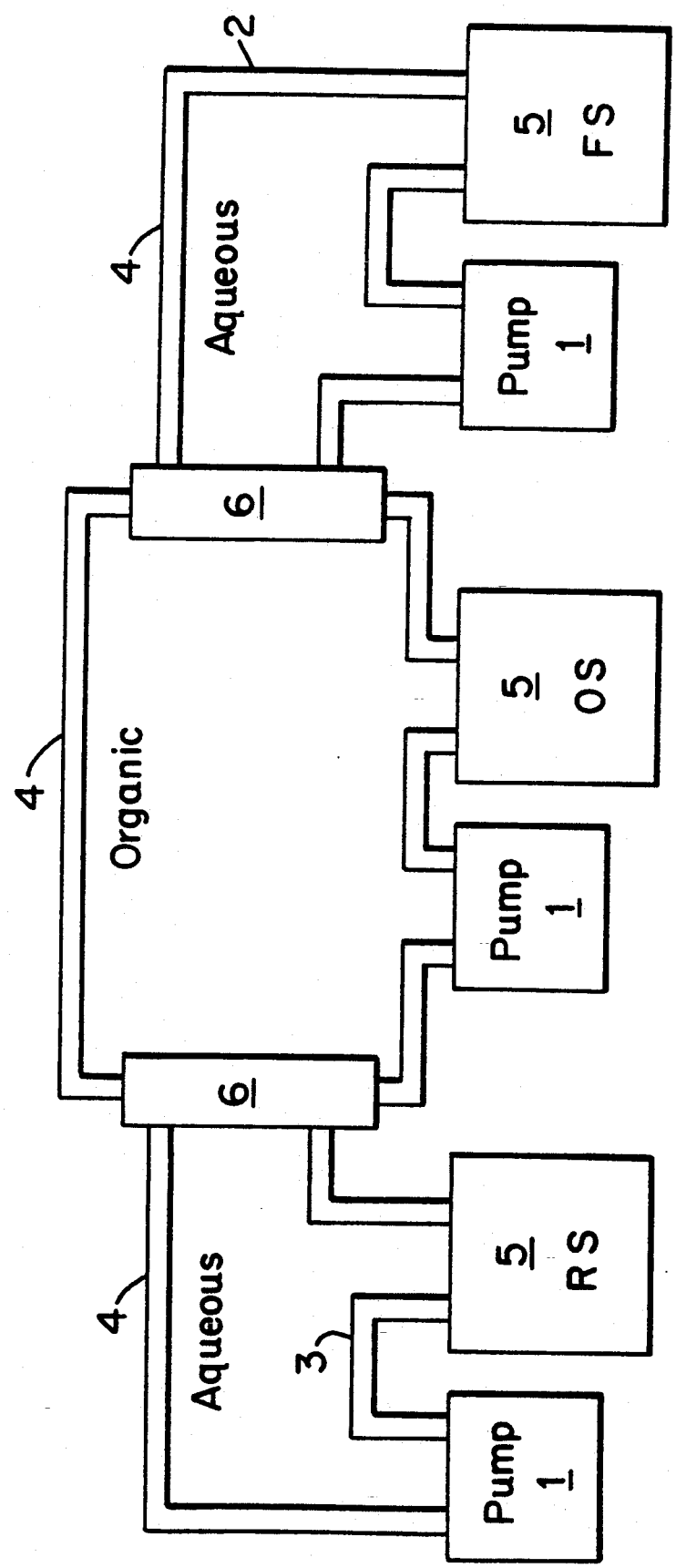

EXTRACTION PROCESS USING A NOVEL ORGANIC ACID AS A LIQUID ION EXCHANGER

This application is a continuation of application Ser. No. 07/700,402, filed May 15, 1991, now abandoned.

BACKGROUND OF THE INVENTION

Solvent extraction is a technique used to transfer one or more dissolved materials between two immiscible phases, e.g., from an aqueous to an organic phase. Frequently the transfer does not proceed rapidly because the solute dissolved in the first phase may have a very low tendency to partition into the second phase. Often, the solute dissolved in an aqueous phase is essentially insoluble in an organic phase.

BRIEF DESCRIPTION OF THE DRAWING

The Figure is a schematic for the experiments described in Examples XII-XIV.

DESCRIPTION OF THE PRIOR ART WITH REGARD TO LIX

It is known to add a liquid ion exchanger (LIX) to one phase of a multi-phase system so that a dissolved material may be transferred more readily into the other phase and then be separated or recovered therefrom. Sometimes a process of this type is referred to as "facilitated transport" rather than solvent extraction (Del Cerro et al *Chem, Ind.*, 1988, 681). However, in this application, the term "solvent extraction" will be used.

Typically, liquid ion exchangers will be used in systems in which one or more materials, e.g., reaction products, are dissolved in an aqueous media and where such materials are not readily soluble in an organic phase used to separate the reaction products from the reaction medium. This technique has been well known by chemists as a tool for laboratory synthesis and now the advantages of liquid ion exchangers for industrial-scale production have been recognized. As a result, liquid ion exchangers are currently employed in the manufacture of chemicals, pharmaceuticals, and the like.

Specifically, an acidic LIX is used to extract an organic base and this enhances the partition of the base into the organic phase and provides a basis for selectivity of separation from other neutral or acidic components.

Solvent extraction involving phase transfer can be conducted in a plurality of systems. One example is a mixed or dispersed-phase system wherein two-phases, one containing a liquid ion exchanger or LIX, are admixed in a tank or other vessel to form an agitated interface or a dispersion. See, for example, U.S. Pat. No. 4,595,571 to Galik, the disclosure of which is incorporated herein by reference. Usually, the overall rate of transfer initially increases with agitation, since increased agitation causes the formation of greater numbers of smaller drops with higher interfacial areas. Ultimately, however, the transfer rate plateaus even if the amount of agitation is increased. Unfortunately, a number of problems are associated with the small drop sizes required to maximize the phase transfer rates. In particular, some LIXs are surface-active by their very nature and act as effective emulsification agents. While this is an advantage where dispersion and the creation of high interfacial areas are the objectives, it is a decided disadvantage when it comes time for the phases to coalesce and be separated from one another. In addition to the practical difficulties associated with the continual making and breaking of dispersions and emulsions, and recovery of products therefrom, incomplete phase separation and entrainment of one phase into the other can result in loss of expensive product and liquid ion exchanger, as well as reduced product purity.

Other disadvantages of conducting a phase transfer operation in a dispersed-phase system is its irreproducibility and relative inflexibility. For example, in a conventional phase transfer operation, one is constrained to operate over relatively narrow ranges of volumetric phase ratios, and the relative mass transfer resistances of the aqueous and organic boundary layers cannot be readily and independently controlled. Scale-up of multiphasic systems is often unreliable as well. With conventional dispersed-phase LIX processing, there is relatively little way of independently manipulating boundary layer to bulk phase volume ratios, interfacial area to bulk phase volume ratios, and absolute and relative aqueous-phase and organic-phase mass transfer resistances in order to improve the efficiency of the liquid ion exchangers utilized.

Other systems employed in solvent extraction utilize membranes to separate an aqueous phase from an organic phase employed in the transfer operations. See, for example, U.S. Pat. Nos. 3,956,112 to Lee et al, 3,957,504 to Ho et al and 4,800,162 to Matson, the disclosures of which are incorporated herein by reference. However, the use of liquid ion exchangers during the membrane solvent extractions described therein is not disclosed. Such membrane solvent extraction operations also leave much to be desired. For example, the aqueous/organic phase partition coefficients are usually unsatisfactory without the use of a LIX in the organic phase thereby making the transfer of the solute from the aqueous phase to the organic phase ineffective.

U.S. Pat. No. 4,523,998 to Kim, the disclosure of which is also incorporated by reference, teaches the use of liquid ion exchangers, e.g., carboxylic acids, in processes to soften water and recover minerals dissolved therein. The use of membranes, e.g., hollow fibers, is also disclosed.

Accordingly, there is a continuing and growing interest in the development of materials which exhibit properties which would markedly improve solvent extraction operations.

There is also a continuing and growing interest in the development of materials suitable for use as liquid ion exchangers which are found to solve the problems encountered in bi- or multi-phase solvent extractions or at least greatly improve such operations.

Accordingly, it is an object of this invention to provide novel organic acids which exhibit utility as liquid ion exchangers in solvent extraction operations.

It is another object of this invention to provide organic acids which, when incorporated therein, will enhance the effectiveness of an organic phase utilized in a solvent extraction operation.

It is another object of this invention to use the LIX to transfer organic bases including nicotine and tobacco alkaloids from an aqueous process stream to another fluid.

It is another object of this invention to provide a method for carrying out solvent extraction operations without the problems associated with the mixing of dispersed phase systems.

It is a further object of this invention to enhance the separability of the phase components per se and reaction products contained therein from the organic base transferred, especially in multi-phased systems.

It is an additional object of this invention to provide reliable, reproducible and controllable solvent extraction separations which are capable of meeting the requirements of efficient industrial processing.

Other objects and advantages of the present invention shall become apparent from the accompanying description and examples.

As used herein, the term "liquid ion exchanger" refers to chemical compounds, for example, organic-phase soluble organic acids, whose addition to one phase of a bi- or multi-phase system, assists in the transfer of a material across the interface and into the other phase, for example, the transfer of an aqueous-soluble organic base from an aqueous phase across the interface and into the organic phase.

DESCRIPTION OF THE INVENTION (1) Novel Liquid Organic Acids

One or more objects of the present invention are accomplished by providing novel organic acids which are characterized by the formula:

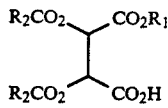

where $R_1$ is a $C_2$–$C_{11}$ linear alkyl group and $R_2$ is a $C_1$–$C_{11}$ linear alkyl group and/or, $R_1$ and/or $R_2$ is a $C_3$–$C_{16}$ branched alkyl group.

Illustrative of $R_1$ and/or $R_2$ linear alkyl substituents are ethyl, propyl, butyl, pentyl, hexyl, heptyl, octyl, nonyl, decyl and undecyl.

Illustrative, but non-limiting, examples of the $R_1$ and/or $R_2$ branched alkyl substituents are isopropyl, 2-methylpropyl, sec-butyl, tert-butyl, 1-ethylpropyl, 2-methylbutyl, 3-methylbutyl, tert-pentyl, 2-methylpentyl, 3-methylpentyl, 4-methylpentyl, 2,2-diethylbutyl, 2,3-dimethylbutyl, 3,3-dimethylbutyl, 2-ethylbutyl, 1-methylhexyl, 2-methylhexyl, 3-methylhexyl, 4-methylhexyl, 5-methylhexyl, 2,2-dimethylpentyl, 2,4-dimethylpentyl, 2,3,3-trimethylbutyl, 1-ethylhexyl, 2-ethylhexyl, 2-isopropyl-5-methylhexyl, 1-methylpentyl, 4-methylheptyl, 6-methylheptyl, and 1-methyl-2-ethylheptyl.

In another aspect, the present invention provides novel liquid ion exchangers characterized by the formula:

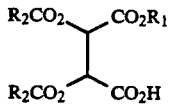

where $R_1$ and/or $R_2$ is a $C_1$–$C_{12}$ linear alkyl group and/or $R_1$ and/or $R_2$ is preferably a $C_3$–$C_{16}$ branched alkyl group.

When employed as a liquid ion exchanger, it has been found that increasing the mass of the $R_1$ and $R_2$ groups of the organic acid increased the lipophilicity and increased the hydrophobicity properties of the compound which enhances its solubility in the organic solution phase (OS) and avoids emulsions. Accordingly, the larger chain alkyl groups, e.g., $C_6$–$C_{11}$ alkyl groups are preferred.

It has also been found that increasing the branching in the $R_1$ and/or $R_2$ groups decreases the emulsification properties when used as a liquid ion exchanger and thus the $C_3$–$C_{16}$ branched alkyl groups are generally preferred over the linear alkyl groups, especially the lower linear alkyl groups.

The most preferred organic acids when employed as LIX in accordance with the present invention are where $R_1$ and $R_2$ are branched $C_6$–$C_{16}$ groups.

(2) Synthesis of Organic Acids

The preparation of a present invention organic acid is illustrated by the following flow diagram:

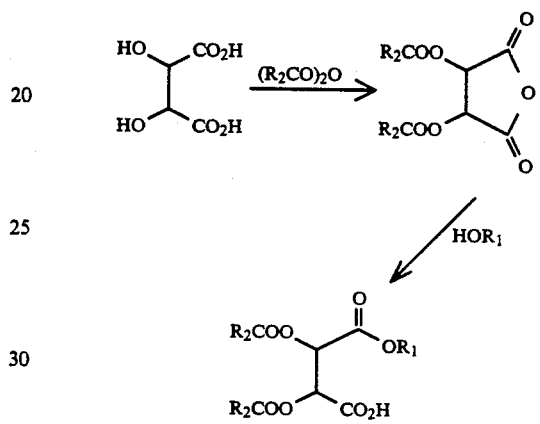

where $R_1$ and $R_2$ are alkyl groups as hereinbefore defined. The reactions per se and the conditions utilized therein are known in the art. Such reactions are further illustrated in the examples herein.

(3) Background of the Prior Art with Regard to Novel Liquid Organic Acids

Lomoelder et al, *Angew. Chem.*, 1987 99, 1282, teach a liquid organic acid wherein both $R_1$ and $R_2$ are $CH_3$.

Huebner et al, *Z. Chem.*, 1968, 8, 380, also teach an organic acid wherein both $R_1$ and $R_2$ are $CH_3$ and its use in the separation of racemic steroids as a resolving agent.

Lucas et al, *J. Am. Chem Soc.*, 1941, 63, 1653, also teach organic acids wherein both $R_1$ and $R_2$ are $CH_3$ as well as compounds wherein $R_1$ can be ethyl, isopropyl or isobutyl with $R_2$ being $CH_3$.

Kolasa et al, *Tetrahedron*, 1989, 45, 3071, teach an organic acid wherein $R_1$ is $CH_2$phenyl with $R_2$ being $CH_3$.

Uray et al, *Tetrahedron*, 1988, 44, 4357, teach organic acids wherein $R_1$ is $C(CH_3)_3$ and $R_2$ is $CH_3$ as well as $R_1$ being $C(CH_3)_3$ when $R_2$ is phenyl.

Duhamel et al, *Bull Soc. Chim. Fr.*, 1982, 75, teach an organic acid wherein $R_1$ is $CH_3$ and $R_2$ is $C(CH_3)_3$.

Netherlands Application NL 6614853 (Apr. 24, 1967) teaches an organic acid of the formula

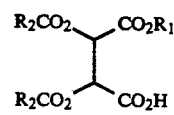

wherein $R_1$ is $CH_3(CH_2)_{10}$ and $R_2$ is $CH_3$ as well as containing a generic disclosure

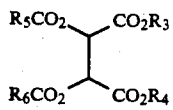

wherein $R_3$ and $R_4$ are hydrogen or alkyl, hydroxyalkyl, acyloxy or acrylpolyethoxy having 2–22 carbon atoms and $R_5$ and $R_6$ are either hydrogen or $C_2$–$C_4$ acyl.

However, none of the prior art disclosed the specific liquid organic acids claimed herein.

(4) Liquid Ion Exchangers in Solvent Extractions

The present invention also pertains to a method of carrying out a solvent extraction in a multi-phase system, such as with aqueous and organic phase(s), wherein one of the phases contains at least one of the liquid ion exchangers or LIX previously described. In the solvent extraction of the present invention, the transfer of the solute(s) which is initially present in one of the separate and immiscible phases, is facilitated by the use of the particular liquid ion exchanger. This invention encompasses the use of certain liquid ion exchangers to accelerate, for instance, the rate of transfer of a water-solubilized reaction product into an organic solvent phase.

The present invention is based, in part, upon the fact that certain compounds, such as the organic acids as defined herein, can effectively aid in the transfer of materials between distinct liquid phases, that is, across their interface. Consider the situation when the solute, e.g., reaction product, is basic and is dissolved in the aqueous phase which is in intimate contact with the organic phase. In the absence of the LIX, the solubility of the basic product in the organic phase can be so small such that negligible transfer rates are observed. However, the presence of the LIX of this invention in the organic phase promotes the transfer of the base into the organic phase and by this mechanism, the transfer is allowed to proceed at a significantly higher rate. Even if the base is soluble in both phases, the presence of the LIX will enhance the transfer rate from the aqueous to the organic phases. In both situations, properly chosen LIX can increase the phase partition coefficient between the organic phase and the aqueous phase.

In general, liquid ion exchangers are acidic in nature and when in the presence of bases, the two will form a stable complex which, with the appropriately chosen LIX, is organic soluble. The degree to which the complex is soluble in the organic phase will depend, among other things, on the nature of the base, the LIX, and the complex (sometimes called a charge transfer complex or an ion-pair), concentration of each species, temperature, and the volume of both the aqueous and organic phases, the nature of the organic phase and other components in the system. The liquid ion exchangers contemplated herein are essentially water insoluble.

It should be noted that the nature of the phases generally employed are two immiscible liquid phases, one organic and the other aqueous. These are characterized, however, by a small but finite solubility of each phase within the other. Since the small amount of either phase dissolved in the other phase has minor or no influence on the overall transfer process, such solvent- or water-saturated phases will be referred to as being "substantially free" of the other phase, thus denoting the absence of significant quantities of one phase being dispersed or entrained within the other.

This invention also provides for the use of a liquid ion exchanger capable of complexing with one or more reaction products which are dissolved in a first liquid aqueous phase and transferring such reaction product into a second liquid organic phase which is substantially immiscible in the first phase, and which by this invention is separated from said first phase by a membrane.

This invention can also be generally stated to be a process for conducting extractions in a liquid-liquid system containing an aqueous phase and an organic phase, said extraction being carried out in the presence of a liquid ion exchanger, the improvement comprising separating said aqueous phase and organic phase with a membrane, which membrane is substantially wet by one of the phases and wherein the organic phase contains a LIX and whereby said aqueous phase and organic phase remain substantially separated by said membrane during and after completion of said extraction process.

This invention is capable of being carried out using membranes having a variety of forms and configurations. For instance, the use of hollow-fiber and other types of membrane systems as two-phase contactors and reactors is particularly suited to and preferred in the conduct of the transfer operation.

In particular, hollow-fiber membrane modules permit intimate, high-surface-area contact to be achieved between the immiscible phases on either side of the membrane, thereby obviating the need to disperse one phase in the other. As a result, entrainment and/or emulsification are minimized or eliminated, these problems otherwise being aggravated by the surface activity of certain liquid ion exchangers. Benefits accrue in terms of rate of product transfer, product recovery or yield, product purity, and overall process effectiveness. Additionally, membrane contacting equipment is simple, reliable, and relatively easily scaled-up as compared to other high-performance phase contacting/separating equipment. Finally, additional operating flexibility is gained in terms of the range of permissible organic/aqueous phase ratios or flow rate ratios.

Another object of this invention is accomplished by providing an efficient industrial membrane solvent extraction process. Broadly, the liquid ion exchanger of the invention, i.e., the organic acids defined herein can be utilized in any solvent extraction system wherein an organic soluble water insoluble LIX can be utilized, especially with any membrane solvent extraction system.

For the organic solvent, it is preferred to use liquid hydrocarbons such as hexane, decane, isoparaffins, aromatics, etc.

In a general sense, an acidic LIX of this invention can, in principle, be used to remove any organic base material, e.g., pyridine, ammonia, amines and the like from dilute aqueous solutions. The utility of the present liquid ion exchangers, however, is especially applicable to the separation of nicotine or the tobacco alkaloids. While most of the examples herein relate to the extraction of nicotine, the overall utility of a present LIX is not limited to the nicotine or tobacco alkaloids.

The extraction of nicotine and related tobacco alkaloids from one tobacco processing fluid to another is an important and difficult technical challenge, especially if this is to be accomplished to the exclusion of transfer of other materials from the original reaction/feedstock (FS) solution to the final extraction/recovery solution (RS).

One membrane extraction process scheme suitable for extracting nicotine from an aqueous reaction solution involves a three-phase system, viz. feed aqueous (FS)/organic extract (OS)/aqueous (RS) solution system, wherein each phase is separated by a membrane. In operation, the feedstock (FS) phase contains nicotine, possibly other tobacco alkaloids, possibly other tobacco constituents, in a dilute aqueous solution. The middle solution phase, containing an organic solvent (OS), is required to separate the FS from the RS membrane layers; thus, the OS is essentially a water barrier. The recovery solution (RS) phase will contain water and sufficient strong acid, e.g., sulfuric acid, to drive a nicotine flux from the FS and OS to the RS.

For the above system to extract nicotine, nicotine must first pass through the OS. To facilitate this process, the organic soluble, water insoluble, liquid ion exchanger (LIX) of the present invention is used in the OS. The LIX must have specific properties for the process to function properly in the membrane extraction of a base such as nicotine, and other constituents, viz.:

(1) The LIX is an organic acid defined herein, to facilitate the flux, e.g., nicotine from the FS to the OS;

(2) However, the LIX cannot be too strong of an acid, since it must allow a nicotine flux from the OS to the RS;

(3) The LIX should have minimum transfer to either the FS or the RS;

(4) The LIX must not cause phase mixing or emulsification;

(5) The LIX must be stable to the extraction conditions;

(6) The LIX should be convenient, safe, and economical to prepare in large quantities; the LIX should be readily disposable;

(7) There should be no transfer of either water from the FS and/or RS to OS; there should be no transfer of OS into either FS or RS; and (8) Analytical tools should be available, or capable of being developed, to quantify the LIX in the membrane system solutions.

Accordingly, the objects of this aspect of the invention are met by the class of liquid ion exchanger having the general structure as defined herein. It is again mentioned that increased branching in the $R_1$ and/or $R_2$ group(s)

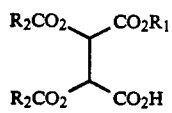

decreases the emulsification properties of the LIX. Further, increasing the size of the $R_1$ and $R_2$ groups increases the lipophilicity and increases the hydrophobicity. Of the LIX utilized, accordingly, a preferred material is the mono(2'-ethylhexyl) 2,3-bis(2-ethylhexanoyloxy)butanedioate, the preparation of which is illustrated in Example X herein.

Although this invention has been described with particular emphasis when $R_1$ and $R_2$ are linear or branched alkyl groups, another embodiment of the invention resides in those situations wherein $R_1$ is an oxygenated alkyl group and $R_2$ is as previously defined.

The expression, "oxygenated alkyl group" is intended to mean $-CH_2CHOHCH_2OCOR$ wherein R is an alkyl group of from 2-20 carbon atoms.

Some compounds of this type are known in the literature but have not been disclosed as LIX agents. Thus, the compound

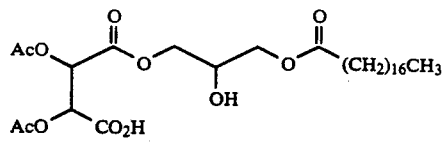

is known as PANADAN SD which is used as a dough conditioner.

Compounds containing an oxygenated alkyl group are less preferred as will be illustrated in Example XII.

Examples of the novel organic acids, their preparation and process, according to this invention, are given hereafter. These examples are meant to be illustrative and not to be considered as limiting the scope of the invention.

EXAMPLE I (2R,3R)-Monodecyl 2,3-Bis(acetyloxyl)butanedioate

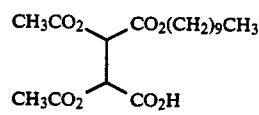

A mixture of 40 g (0.185 mol) of diacetyl tartaric anhydride and 44.85 g (0.185 mol) of 1-decanol was heated and stirred under a nitrogen atmosphere at a temperature of 130° C. for 3 hours. The product was cooled to room temperature, taken up in chloroform, washed with brine three times, dried ($Na_2SO_4$) and filtered. The resulting clear solution was concentrated at high vacuum (120° C./0.01 torr.) to give 52.3 g (75.4% yield) of the above titled compound as a light amber colored oil.

A solution in $CDCl_3$ of the above product was analyzed by Nuclear Magnetic Resonance (NMR spectroscopy which confirmed the structure thereof.

$^1H$ NMR ($CDCl_3$) δ 0.88 (t, 3H, J=7.0 Hz), 1.43 (br s, 16H), 1.58 (m, 2H), 2.17 (s, 3H), 2.20 (s, 3H), 4.13–4.23 (m, 2H), 5.72 (d, 1H, J=2.7 Hz), 5.76 (d, 1H, J=2.7 Hz). $^{13}C$ NMR ($CDCl_3$) δ 14.32, 20.44, 20.54, 22.88, 25.82, 28.59, 29.32, 29.46, 29.70, 32.06, 66.71, 70.55, 70.86, 84.10, 165.86, 169.75, 169.94, 170.24.

Calc. for $C_{18}H_{30}O_8$ : C, 57.74; H, 8.08.
Found: C, 57.60; H, 8.08.

EXAMPLE II (2R, 3R)-Monohexadecyl 2,3-Bis(acetyloxy)butanedioate

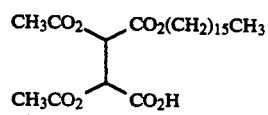

A mixture of 40 g (0.185 mol) of diacetyl tartaric anhydride and 44.85 g (0.185 mol) of cetyl alcohol was heated and stirred under a nitrogen atmosphere at 130° C. for 3 hours. The resulting clear amber colored oil was cooled to room temperature and after taken up in chloroform, washed with brine three times, dried (Na₂SO₄) and filtered. The resulting clear solution was concentrated at high vacuum (120° C./0.01 torr.) to give 73.8g (87% yield) of the above titled compound.

A solution in CDCl₃ of the above product was analyzed by Nuclear Magnetic Resonance (NMR) spectroscopy which confirmed the structure thereof.

$^1$H NMR (CDCl₃) δ 0.88 (t, 3H, J=7.0 Hz), 1.26 (br s, 26H), 1.62 (m, 2H), 2.17 (s, 3H), 2.20 (s, 3H), 4.13–4.20 (m, 2H), 5.71 (d, 1H, J=2.7 Hz), 5.76 (d, 1H, J=2.7 Hz). $^{13}$C NMR (CDCl₃) δ 14.14, 20.25, 20.35, 22.70, 25.63, 28.40, 29.14, 29.36, 29.56, 29.68, 31.90, 66.51, 70.35, 70.60, 165.59, 169.48, 169.69, 170.38 (some resonance signals involve more than one carbon atom).

Calc for $C_{24}H_{42}O_8$: C, 62.85; H, 9.23.
Found: C, 63.04; H, 9.52.

EXAMPLE III (2R, 3R, 2'R)- and (2R, 3R, 2'S)-Mono(2'-Ethylhexyl) 2,3-Bis(acetyloxy)butanedioate

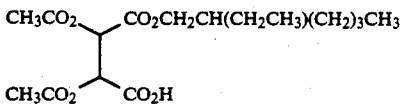

The above titled material was prepared in the exact same manner and scale as described in Example II with 40.0 g (0.185 mol) of diacetyl tartaric anhydride and 24.1 g (0.185 mol) of 2-ethyl-1-hexanol to give 51.4 g (80.2% yield) of the said material as a mixture of diastereomers.

A solution in CDCl₃ of the above product was analyzed by Nuclear Magnetic Resonance (NMR) spectroscopy which confirmed the structure thereof. $^1$H NMR (CDCl₃) δ 0.82–0.92 (m, 6H), 1.73–1.38 (m, 7H), 1.52–1.61 (m, 2H) 2.16 (s 3H) 2.20 (s, 3H), 2.20 (s, 3H), 4.04–4.22 (m, 2H), 5.76 (s, 2H). $^{13}$C NMR (CDCl₃) δ 10.83 and 10.97, 14.05, 20.27, 20.35, 22.93, 23.60, 28.86 and 28.94, 30.19 and 30.30, 38.69 and 38.78, 68.58, 70.63, 70.84, 169.91, 170.05, 170.10.

Calc. for $C_{16}H_{26}O_8$: C, 55.48; H, 7.57.
Found: C, 55.47; H, 7.28.

EXAMPLE IV (2R, 3R)-Monooctyl 2,3-Bis(propionyloxy)butanedioate

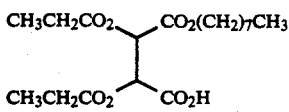

Using the same procedure described in Example I, 17.7 g (72.4 mmol) of dipropionyl tartaric anhydride and 9.4 g (72.4 mmol) of 1-octanol gave 23.0g (84.8% yield) of the above titled compound.

A solution in CDCl₃ of the above product was analyzed by Nuclear Magnetic Resonance (NMR) spectroscopy which confirmed the structure thereof. $^1$H NMR (CDCl₃) δ 0.88 (t, 3H, J=6.7 Hz), 1.16 (t, 3H, J=7.6 Hz), 1.17 (t, 3H, J=7.6 Hz), 1.21–1.32 (br s, 12H), 1.60–1.63 (m, 2H), 2.3–2.5 (m, 4H), 4.10–4.20 (m, 2H), 5.71 (d, 1H, J=2.7 Hz), 5.78 (d, 1H, J=2.7). $^{13}$C NMR (CDCl₃) δ 8.87 (2C), 14.08, 22.61, 25.63, 27.03, 28.39, 29.08, 31.72, 66.40, 70.21, 70.48, 165.66, 171.03, 172.93, 173.08.

Analysis. Calc. for $C_{18}H_{30}O_8$: C, 57.74; H, 8.08.
Found: C, 57.55; H, 8.25.

EXAMPLE V (2R, 3R, 2'R)- and (2R, 3R, 2'S)-Mono(2'-Ethylhexyl) 2,3-Bis(propionyloxy)butanedioate

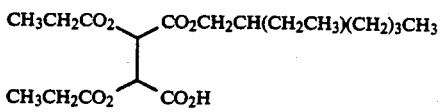

A mixture of 150 g (1.0 mol) of natural L-tartaric acid and 455.5g (3.5 mol) of propionic anhydride was heated and stirred to an initial exotherm and then maintained at 130° C. for 30 minutes. The resulting propionic acid and excess propionic anhydride was removed at reduced pressure. The residue was triturated with ether and the resulting crystals were collected, washed with ether and dried in vacuum to give 120 g (49% yield) of colorless dipropionyl tartaric anhydride, mp 71°–3° C. This material was used directly in the next step.

The same procedure as described in Example I using 20.0 g (81.9 mmol) of the dipropionyl tartaric anhydride and 10.66g (81.9 mmol) of (R, S)-2-ethyl-1-hexanol, was carried out and gave 27.8 g (90.6% yield) of the above titled material as a light amber colored oil.

A solution in CDCl₃ of the above product was analyzed by Nuclear Magnetic Resonance (NMR) spectroscopy which confirmed the structure thereof.

$^1$H NMR (CDCl₃) δ 0.84–0.93 (m, 6H), 1.18 (t, 3H, J=7.4 Hz), 1.19 (t, 3H, J=7.4 Hz), 1.23–1.40 (m, 9H), 1.56–1.61 (m, 1H), 2.36–2.54 (m, 4H), 4.05–4.19 (m, 2H), 5.73–5.78 (m, 2H). $^{13}$C NMR (CDCl₃) δ8.82, 10.90, 10.92, 14.00, 22.87, 23.52, 26.96, 8.81, 30.22, 38.58, 38.68, 68.36, 70.29, 70.51, 165.80, 170.71, 172.92, 173.08.

Calc. for $C_{18}H_{30}O_8$: C, 57.74; H, 8.08.
Found: C, 57.49; H, 7.85.

EXAMPLE VI (2R, 3R, 1'R)- and (2R, 3R, 1'S)-Mono (1'-Methylheptyl) 2,3-Bis(propionyloxy)butanedioate

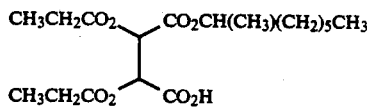

Using the same procedure described in Example I with 21.0 g (0.086 mol) of dipropionyl tartaric anhydride prepared as described in Example V and 11.2g (0.086 mol) of (R,S)-2-octanol gave 28.3g (88% yield) of the above titled material as a mixture of diastereomers as a light amber colored oil.

A solution in CDCl₃ of the above product was analyzed by Nuclear Magnetic Resonance (NMR) spectroscopy which confirmed the structure thereof. $^1$H NMR (CDCl₃) δ 0.86 (t, 3H, J=7.0 Hz), 0.88 (t, 3H, J=6.9 Hz), 1.16 (t, 3H, J=7.6 Hz), 1.17 (t, 3H, J=7.8 Hz), 1.17 (t, 3H, J=7.6 Hz), 1.24–1.28 (m, 9H), 1.45–1.60 (m, 2H), 2.36–2.54 (m, 4H), 4.93–5.00 (m, 1H), 5.69 (d, ½ H, J=2.7 Hz), 5.70 (d, ½ H, J=2.7 Hz), 5.76 (d, ½ H, J=2.7 Hz), 5.80 (d, ½ H, J=2.7 Hz). $^{13}$C NMR (CDCl₃) δ 9.41 and 9.49 (2C), 14.69, 20.23 and 20.44, 23.22, 25.80, 27.59 and 27.71 (2C), 29.68, 32.28 and 32.32, 36.29, 70.94 and 71.09, 71.31 and 71.35, 74.63 and 74.71, 166.18, 171.68, 173.85, 174.06.

Anal Calc. for $C_{18}H_{30}O_8$ : C, 57.74; H, 8.08.
Found: C, 57.44: H, 8.08.

EXAMPLE VII (2R, 3R, 1'R)- and (2R, 3R, 1'S)-Mono(1'-Ethylhexyl) 2,3-Bis(propionyloxy)butanedioate

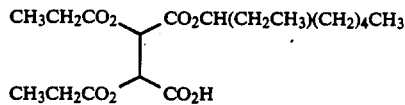

Using the same procedure as described in Example I with 15.2 g (62.2 mmol) of dipropionyl tartaric anhydride prepared as described in Example V and 8.11 g (62.2 mmol) of (R,S)-3-octanol gave 21.8 g (93.5% yield) of the above titled material as a mixture of diastereomers as an oil.

A solution in CDCl$_3$ of the above product was analyzed by Nuclear Magnetic Resonance (NMR) spectroscopy which confirmed the structure thereof. $^1$H NMR (CDCl$_3$) δ 0.75 (m, 6H), 1.03–1.24 (m, 12H), 1.32–1.59 (m, 4H), 2.29–2.51 (m, 4H), 4.80–4.89 (m, 1H), 5.66–5.69 (m, 1H), 5.70–5.73 (m, 1H), 9.6–9.9 (br s, 1H). $^{13}$C NMR (CDCl$_3$) δ 8.79, 8.82, 8.91, 8.93, 9.31, 9.49, 14.03, 22.54, 22.57, 24.86, 24.90, 26.80, 26.97, 27.08, 27.14, 27.16, 31.69, 31.73, 33.45, 70.63, 70.67, 70.86, 70.90, 78.64, 166.01, 169.92, 173.38, 173.47, 173.55, 173.58.

H, 8.08.
Anal. Calc. for $C_{18}H_{30}O_8$ : C, 57.74; H, 8.08.
Found: C, 57.49; H, 7.85.

EXAMPLE VIII (2R, 3R 1'ξ, 2'ξ)-Mono(1'-Methyl-2'-Ethylhexyl) 2,3-Bis(propionyloxy)butanedioate

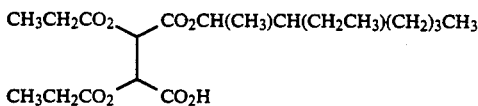

Using the same procedure described in Example I with 6.09 g (65.5 mmol) of dipropionyl tartaric anhydride prepared as described in Example V and 9.43 g (65.5 mmol) of 3-ethyl-2-heptanol gave 23.5 g (92.6% yield) of the above titled material and as a mixture of diastereomers as an amber colored oil.

A solution in CDCl$_3$ of the above product was analyzed by Nuclear Magnetic Resonance (NMR) spectroscopy which confirmed the structure thereof. $^1$H NMR (CDCl$_3$) δ 0.81–0.94 (m, 6H), 1.10–1.45 (m, 16H), 2.32–2.54 (m, 4H), 5.02–5.13 (m, 1H), 5.67–5.80 (m, 2H).

Anal. Calc. for $C_{19}H_{30}O_8$ : C, 58.74; H, 8.30.
Found: C, 58.49; H, 8.33.

EXAMPLE IX (2R, 3R, 2'R)- and (2R, 3R, 2'S)-Mono(2'-Ethylhexyl) 2,3-Bis(pentanoyloxy)butanedioate

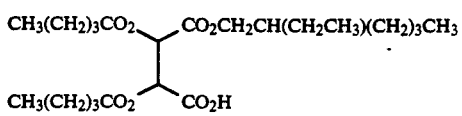

A mixture of 23.0 g (0.153 mol) of natural L-tartaric acid and 100 g (0.537 mol) of valeric anhydride was heated and stirred for 30 minutes at 130° C. The mixture was then cooled and concentrated under reduced pressure (bp 70° C./0.05 torr.) followed by cooling to induce crystallization. Trituration with cold hexane followed by collection of the product by filtration gave 13.55 g (29.5% yield) of colorless divaleroyl tartaric anhydride which was used directly in the next step.

The same procedure was used as described in Example I with 13.55 g (0.045 mol) of divaleroyl tartaric anhydride and 5.88g (0.045 mol) of (R,S)-2-ethylhexanol and gave 17.15 g (88.3% yield) of the above titled material as a mixture of diastereomers as an oil.

A solution in CDCl$_3$ of the above produce was analyzed by Nuclear Magnetic Resonance (NMR) spectroscopy which confirmed the structure thereof.

$^1$H NMR (CDCl$_3$) δ 0.84–0.92 (m, 12H), 1.17–1.43 (m, 12H), 1.50–1.60 (m, 5H), 2.30–2.52 (m, 4H), 3.98–4.18 (m, 2H), 5.82–5.87 (m, 2H). $^{13}$C NMR (CDCl$_3$) δ 10.60, 10.69, 10.76, 13.42, 13.81, 21.88, 22.70, 23.32, 26.32, 26.53, 28.64, 29.93, 30.01, 33.13, 33.18, 38.42, 38.50, 68.30, 70.15, 70.40, 165.88, 170.80, 172.30, 172.38, 172.48.

Anal. Calc. for $C_{22}H_{38}O_8$ : C, 61.37; H, 8.90.
Found: C, 61.33; H, 8.90.

EXAMPLE X (2R, 3R, 2'ξ, 2''ξ, 2'''ξ)-Mono(2'-Ethylhexyl) 2,3-Bis(2-ethylhexanoyloxy)butanedioate

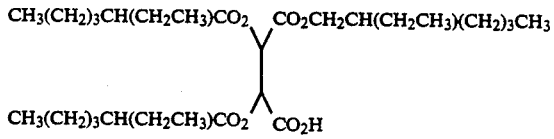

A mixture of 87.1 g (0.322 mol) of 2-ethylhexanoic anhydride and 13.8 g (0.092 mol) of L-tartaric acid was heated and stirred at a temperature of about 140°–145° C. for 30 minutes to give a clear solution. Heating was continued for an additional 30 minutes at about 130°–135° C. The volatiles were then removed at reduced pressure (120° C./0.01 torr.) to give 38 g of di(2-ethylhexanoyl)tartario anhydride which was used in the next step without further purification.

A mixture of 38.3 g (0.104 mol) of the crude anhydride was mixed with 12.9 g (0.099 mol) of 2-ethyl-1-hexanol and was heated and stirred for 3 hours at 125°–130° C. Work up was the same as described in Example I to give 43.7 g (88.5% yield) of the above titled material as a mixture of diastereomers as an amber colored oil.

A solution in CDCl$_3$ of the above product was analyzed by Nuclear Magnetic Resonance (NMR) spectroscopy which confirmed the structure thereof.

$^1$H NMR (CDCl$_3$) δ 0.82–0.95 (m, 18H), 1.18–1.69 (m, 25H), 2.35–2.42 (m, 2H), 3.96–4.13 (m, 2H), 5.70–5.76 (m, 2H). $^{13}$C NMR (CDCl$_3$) δ 10.84, 11.40, 11.55, 11.62, 13.86, 13.93, 14.05, 22.60, 22.63, 22.97, 23.48, 23.54, 25.16, 25.22, 25.27, 28.82, 28.88, 29.22, 39.32, 30.12, 31.34, 31.40, 38.59, 38.62, 46.70, 46.88, 68.75, 68.81, 70.18, 70.24, 70.55, 165.90, 172.24, 174.87, 175.06.

Anal. Calc. for $C_{28}H_{50}O_8$ : C, 65.34; H, 9.79.
Found: C, 65.13; H, 9.58.

EXAMPLE XI

As hereinbefore disclosed, two different experimental criteria can be used to measure the capability of a LIX. First, the organic phase/water phase partition coefficient (PC) can be determined. The partition coefficient, as used herein, can be defined as the ratio of the amount of a substance dissolved in one phase in relation to the amount of the substance dissolved in the second phase. Accordingly, in determining the partition coefficient in the solvent extraction of nicotine from a tobacco processing fluid to another, the ratio would be the concentration of nicotine in the organic (extraction) phase divided by the concentration of nicotine in the aqueous (process) phase. If the partition coefficient increases, i.e., more of the nicotine is soluble in the organic phase, in the presence of a LIX, then this LIX meets one of the objectives for a successful nicotine transfer agent.

Table I is a presentation of the partition coefficients of various liquid ion exchangers, including control experiments where no LIX are utilized. It is noteworthy that the partition coefficient for the LIX from Examples III and V is less than without any LIX present, indicating that the nicotine-LIX complex for these two LIX is more water soluble than hexane soluble. This data indicates that partition coefficients are physical characteristics which must be considered carefully for modeling and scaling up membrane separation systems. Capabilities of the LIX as well as the components of the various phases must all be considered.

TABLE I

Partition Coefficients (PC) for Various Liquid Ion Exchangers

| Run No. | LIX | Solvent[a] | PC[b] |
|---|---|---|---|
| 1 | None | I | 0.13 |
| 2 | Panodan SD | I | 11.5 |
| 3 | Example III | I | <0.1 |
| 4 | Example V | I | 4.4 ± 1.0 |
| 5 | Example IV | I | 1.8, 2.5 |
| 6 | None | H | 1.12 |
| 7 | Example III | H | 0.43 |
| 8 | Example V | H | 0.51 |
| 9 | Example IX | H | 1.40 |
| 10 | Example X | H | 2.90 |

[a]H - hexane; I - Isopar K (an isoparaffinic petroleum solvent marketed by Exxon)
[b]PC - [conc of nicotine in organic phase]/[conc of nicotine in aqueous phase]
Note: $CO_2$-saturated water was utilized in the aqueous phase of Run Nos. 1-5.

EXAMPLE XII

Another of the experimental criteria which can be used to measure the capability of a LIX is the actual extraction efficiency using a membrane system. The efficiency can be experimentally determined, with various LIX and compared against a system without any LIX.

The apparatus used is a Model MSX-750 laboratory unit purchased from Sepracor, Inc., Marlborough, Mass.; it is a 3-panel, 3-loop, 2-membrane operation. As shown in the Figure, each panel has a solvent circulation pump (1), pressure gauge, flow rotometer, and multiple valves for control of the solvent input and output (not shown). A separate pump controller (not shown) provides variable speed and on/off controls for all three panels. Analysis ports are built into the unit to allow pH readings at the feedstock (2)- and recovery panels (3)- and automatic pH titration at the recovery solution panel. Sample aliquots can be removed from all three system solvents in line (4)- or from the reservoirs (5). The membrane modules (6) contain a hollow fiber bundle in a plastic cartridge with connectors to allow flow through the hollow fibers (lumen) with one solvent and simultaneous flow around the fibers (shell) with an "exchanging" solvent (not shown). The membrane fibers used were either regenerated cellulose (RC) or polyacrylonitrile (PAN) and were 0.5-1.5 square meters in surface area.

For this membrane separation process, solutions are recirculated at 100-900 ml/min. The feedstock reservoir volume is between 0.5 L and 8.0 L of aqueous solution which is 0.1-10.0% dissolved base, e.g., pyridine or nicotine, at a pH between 4 and 10. The feedstock solution can also contain other compounds, e.g., tobacco components. The organic solvent (OS) reservoir contains from 300-1000 mL of a water-immiscible solvent like hexane, heptane, octane, nonane, decane or Isopar K (Exxon) to which is added 0.1-10.0% of LIX. The OS is recirculated in the center panel through the lumen of both membrane modules and is always kept at 2-10 psi higher than the aqueous phases to maintain phase separation. The aqueous recovery solution is maintained at a constant pH (1.0-4.0) via an automatic titration unit (Metrohm Model 665 Dosimat with Model 614 Impulsomat and Model 632 Digital-pH-Meter, Metrohm Ltd., CH-9100 Herisau, Switzerland) using 1.0 M sulfuric acid to provide a pH differential and as a collection sink for the base being transferred, e.g., pyridine or nicotine.

For the purpose of comparison, commercially available (from Grindsted) Panodan SD was examined which material has the following structure:

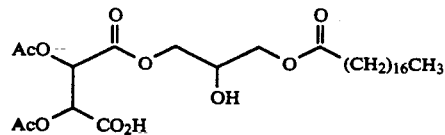

The feedstock (FS) contained pyridine or nicotine in a dilute aqueous solution. In particular, other tobacco alkaloids, and even other tobacco constituents could be extracted. The recovery solution (RS) contained pyridine or nicotine, water, and sufficient sulfuric acid to drive a flux of the base(s) from the FS to the RS. The middle solution contained an organic solvent (OS), required to separate the FS from the RS membrane layers —— the OS is essentially a water barrier. Table II illustrates the Extraction Capacities using this membrane system. The organic solvent (OS) was Isopar K in all extractions.

TABLE II

Membrane-Based Extraction Efficiencies of Nicotine or Pyridine Using Liquid Ion Exchangers

| Run No. | Substrate | LIX (%) | Membrane | Extraction Capacity (g/day-m) |
|---|---|---|---|---|
| 1 | pyridine[a] | Panodan SD (5%) | RC | 3.2 |
| 2 | pyridine[b] | Example IV (5%) | PAN | 5.1 |
| 3 | pyridine[b] | Example V (5%) | PAN | 4.2 |
| 4 | nicotine[b] | None | PAN | 1.2 |
| 5 | nicotine[b] | Example X (2%) | PAN | 8.2 |
| 6 | nicotine[b] | Example X | PAN | 9.8 |

TABLE II-continued

Membrane-Based Extraction Efficiencies of Nicotine or Pyridine Using Liquid Ion Exchangers

| Run No. | Substrate | LIX (%) | Membrane | Extraction Capacity (g/day-m) |
|---|---|---|---|---|
| | | (5%) | | |

RC = regenerated cellulose membranes
PAN = poly(acrylonitrile) membranes
[a]1M NaCl in both FS and RS
[b]CO$_2$-saturated FS While Panodan SD was successful in terms of increasing the organic/water partition coefficient, long-term operation in the membrane system resulted in transfer of the organic phase from OS to both the FS and the RS. This was due to the breakdown of the organic/aqueous interface at the membrane, caused by the excellent emulsifying power of Panodan. It is believed that the glycerol fragment of Panodan SD (i.e., the O—CH$_2$CH(OH)—CH$_2$O moiety) was in part responsible for this breakdown of the organic/aqueous interface. However, pyridine was successfully extracted from a dilute aqueous solution using Panodan as the LIX and regenerated cellulose membrane modules when 1M NaCl was present in both aqueous solutions (see Run No. 1 in Table II).

EXAMPLE XIII

Six consecutive extractions of nicotine were performed with the apparatus utilized in Example XII (1.5 m$^2$ membrane area) with 4 L of 20 mM nicotine in CO$_2$-saturated water as the initial FS with pH adjusted to 7.34 with base, 500 mL of Isopar-K as OS solvent, and 250 mL of deionized water, with pH maintained at 3.0 with the automatic addition of 1M H$_2$SO$_4$ as the RS, using 5% of the organic acid prepared in Example X as the LIX in the OS. The RS was replaced following each extraction. The results are summarized in Table III below.

TABLE III

Summary of Membrane-Based Nicotine Extraction Using Example X as the Liquid Ion Exchanger
Percent (%) remaining in FS

| Run | \multicolumn{6}{c}{Time (min)} | calculated extraction capacity[a] |
|---|---|---|---|---|---|---|---|
| | 15 | 30 | 45 | 60 | 120 | 180 | |
| 1 | 88.6 | 62.8 | 66.1 | 56.5 | 22.1 | 10.0 | 7.8 |
| 2 | 69.7 | 73.9 | 57.8 | 52.4 | 14.7 | ND[c] | 9.2 |
| 3 | 79.8 | 63.5 | 58.1 | 41.8 | 16.8 | ND | 9.2 |
| 4 | 82.7 | 65.2 | 57.8 | 43.6 | 16.3 | ND | 9.2 |
| 5 | 84.1 | 77.8 | NA[b] | 54.9 | 21.5 | ND | 7.6 |
| 6 | 72.8 | 64.2 | 54.6 | 44.0 | 17.1 | ND | 9.1 |

[a]Gal/day treatment capacity at 80% removal of nicotine for 1 m$^2$ membrane
[b]Data not taken
[c]None detected

EXAMPLE XIV

Another example which shows the efficacy of the LIX can be seen in the data of Table IV below. Seven consecutive runs were performed with the apparatus outlined in Example XII without the use of a LIX in the OS, changing to a fresh 1 liter 0.32% nicotine FS each run and leaving the RS alone to concentrate the nicotine recovered (Section A). Prior to run 8, fresh FS, OS and RS solutions were placed within the system. For the five consecutive runs 8-12, 2% LIX (Example X) in Isopar K was used as the OS, 0.32% nicotine in deionized water for FS (one liter fresh for each run), and a fresh deionized water RS was left in place for all five runs to concentrate the nicotine (Section B). The volume of the RS increased during the runs 8-12 because the nicotine was transferred into it and because acid solution was pumped into it to maintain a pH of ca. 3. Then three additional runs 13-15 were made using the same OS and the same RS (to form a more concentrated nicotine solution) from Section B; 4 L FS solutions of 0.32% nicotine in deionized water (a fresh solution each run) were used (Section C). Comparison of Section A with the corresponding data in Section B indicates that the addition of LIX speeds up the facilitated transport of nicotine. Comparison of the data within Section B shows the consistent operation of the system with repeated runs. Comparison of Section B with Section C shows the linear nature of scaling up the feedstock volume. This result suggests the possibility of a "continuous" operation of the system by (a) valving in a fresh feedstock volume when the appropriate nicotine depletion is accomplished and (b) valving in a new RS (or siphoning off volume from the RS) to allow continued acid titration. The OS continues to operate without replacement.

TABLE IV

Membrane-Based Extractions of Nicotine With A) No LIX, B) 2% LIX, and C) 2% LIX scale-up.

Section A. No LIX, 1 liter FS at 0.32% nicotine, 1.5 m$^2$ PAN.

| Run | Percent (%) nicotine remaining in FS 60 min |
|---|---|
| 1 | 27 |
| 2 | 26 |
| 3 | 27 |
| 4 | 28 |
| 5 | 28 |
| 6 | 27 |
| 7 | 25 |

Section B. 2% LIX (Example X) in Isopar K, 1 liter FS at 0.32% nicotine, 1.5 m$^2$ PAN.
Percent (%) nicotine remaining in FS

| Run | 0 min | 15 m | 30 m | 45 m | 60 m |
|---|---|---|---|---|---|
| 8 | 100 | 49 | 37 | 23 | 14 |
| 9 | 100 | 49 | 36 | 24 | 14 |
| 10 | 100 | 50 | 36 | 24 | 13 |
| 11 | 100 | 50 | 37 | 23 | 14 |
| 12 | 100 | 49 | 35 | 23 | 13 |

Section C. 2% LIX (Example X) in Isopar K, 4 liters FS at 0.32% nicotine, 1.5 m$^2$ PAN.
Percent (%) nicotine remaining in FS

| Run | 0 min | 60 m | 120 m | 180 m | 240 m |
|---|---|---|---|---|---|
| 13 | 100 | 51 | 35 | 21 | 13 |
| 14 | 100 | 51 | 37 | 23 | 13 |
| 15 | 100 | 51 | 37 | 23 | 13 |

Note: OS = Isopar K. The RS was kept in place for runs 1-7 and reached a final volume of 260 mL (from 150 mL initially) and a final nicotine concentration of 3.7%.
Note: The RS was kept in place for all eight runs (runs 8-15) in Section B and Section C and reached a final volume of 445 mL (from 150 mL initially) and a final concentration of nicotine of 6.9%.

What is claimed is:

1. An organic acid characterized by the formula:

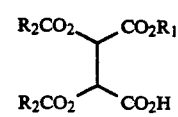

where each of R$_1$ and R$_2$ is a C$_3$-C$_{16}$ branched alkyl group.

2. An organic acid in accordance with claim 1 which is (2R, 3R, 2'ξ, 2"ξ, 2'''ξ)-mono(2'-ethylhexyl) 2,3-bis(2-ethylhexanoyloxy) butanedioate.

3. In a process for conducting a liquid extraction in a system which contains at least one aqueous phase and at least one organic phase and involves the transfer of a solute contained in one phase across an interface and into the adjacent phase, the improvement which comprises including a liquid ion exchanger in the organic phase characterized by the formula:

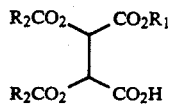

where $R_1$ is a $C_2$–$C_{11}$ linear alkyl group or a $C_3$–$C_{16}$ branched alkyl group and $R_2$ is a $C_1$–$C_{11}$ linear alkyl group or a $C_3$–$C_{16}$ branched alkyl group, and at least one of $R_1$ and $R_2$ is a $C_3$–$C_{16}$ branched alkyl group.

4. A process in accordance with claim 3 wherein the phases are separated by a membrane.

5. A process in accordance with claim 3 wherein the aqueous phase contains a solute selected from the group consisting of nicotine and tobacco alkaloids.

6. A process in accordance with claim 3 wherein $R_1$ is a $C_3$–$C_{16}$ branched alkyl group.

7. A process in accordance with claim 3 wherein each of $R_1$ and $R_2$ is a $C_3$–$C_{16}$ branched alkyl group.

8. A process in accordance with claim 3 wherein the liquid ion exchanger is selected from the group consisting of (2R, 3R, 2'R)- and (2R, 3R, 2'S)-mono(2'-ethylhexyl) 2,3-bis(acetyloxy)butanedioate; (2R, 3R, 2'R)- and 2R, 3R, 2'S)-mono(2'-ethylhexyl) 2,3-bis(propionyloxy)butanedioate; (2R, 3R, 1'R)- and (2R, 3R, 1'S)-mono(1'-methylheptyl 2,3-bis(propionyloxy)butanedioate; (2R, 3R, 1'R)- and (2R, 3R, 1'S)-mono(1'-ethylhexyl) 2,3-bis(propionyloxy)butanedioate; (2R, 3R, 1'ξ, 2'ξ)-mono(1'-methyl-2'-ethylhexyl) 2,3-bis(propionyloxy)butanedioate; and (2R, 3R, 2'R)- and (2R, 3R, 2'S)-mono(2'-ethylhexyl) 2,3-bis(pentanoyloxy)butanedioate.

9. A process in accordance with claim 3 wherein the liquid ion exchanger is (2R, 3R, 2'ξ, 2"ξ, 2'''ξ)-mono(2'-ethylhexyl) 2,3-bis(2-ethylhexanoyloxy)butanedioate.

* * * * *